(12) United States Patent
Cheiky et al.

(10) Patent No.: US 8,236,085 B1
(45) Date of Patent: *Aug. 7, 2012

(54) METHOD FOR ENHANCING SOIL GROWTH USING BIO-CHAR

(75) Inventors: Michael Cheiky, Thousand Oaks, CA (US); Ronald A. Sills, Houston, TX (US); Mark L. Jarand, Newbury Park, CA (US)

(73) Assignee: Cool Planet Biofuels, Inc., Camarillo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/308,801

(22) Filed: Dec. 1, 2011

Related U.S. Application Data (62) Division of application No. 13/154,213, filed on Jun. 6, 2011.

(51) Int. Cl.
| C05F 11/08 | (2006.01) |
| C05D 9/00 | (2006.01) |
| C05D 9/02 | (2006.01) |

(52) U.S. Cl. ............... 71/6; 71/11; 71/31; 71/32; 71/54; 71/63; 71/903; 423/445 R (58) Field of Classification Search .............. 423/445 R; 71/6, 11, 31, 32, 54, 63, 903
See application file for complete search history.

(56) References Cited

U.S. PATENT DOCUMENTS

| 203,016 A | 4/1878 | Edison |
| 222,390 A | 12/1879 | Edison |
| 474,230 A | 5/1892 | Edison |
| 4,268,275 A | 5/1981 | Chittick |
| 4,421,524 A | 12/1983 | Chittick |
| 4,487,958 A | 12/1984 | Ream et al. |
| 4,497,637 A | 2/1985 | Purdy et al. |
| 4,530,702 A | 7/1985 | Fetters et al. |
| 4,861,351 A | 8/1989 | Nicholas et al. |
| 4,992,480 A | 2/1991 | Mahajan et al. |
| 5,032,618 A | 7/1991 | Marchionna et al. |
| 5,087,786 A | 2/1992 | Nubel et al. |
| 5,221,290 A | 6/1993 | Dell |
| 5,504,259 A | 4/1996 | Diebold et al. |
| 5,756,194 A | 5/1998 | Shogren et al. |
| 5,820,640 A | 10/1998 | Ikura et al. |
| 5,857,807 A | 1/1999 | Longo |
| 6,133,328 A | 10/2000 | Lightner |

(Continued)

FOREIGN PATENT DOCUMENTS

| KR | 100819505 | 3/2008 |

(Continued)

OTHER PUBLICATIONS

Z. Rosenberg; "More on Commercial Carbon Resistors as Low Pressure Guages," Intl. Jour. of Impat Eng. 34 (2007) pp. 732-742.

(Continued)

*Primary Examiner* — Wayne Langel
(74) *Attorney, Agent, or Firm* — David E. Heisey; Sheppard Mullin Richter & Hampton (57) ABSTRACT

A method is described for rendering char from a biomass fractionator apparatus (BMF char) suitable for addition to soil in high concentrations, the method relying on multiple processes comprising removing detrimental hydrocarbons from BMF char, removing adsorbed gases from BMF char, introducing microorganisms to the BMF char, and adjusting soil pH.

16 Claims, 11 Drawing Sheets

U.S. PATENT DOCUMENTS

| | | |
|---|---|---|
| 6,227,473 B1 | 5/2001 | Arnold |
| 6,339,031 B1 | 1/2002 | Tan |
| 6,548,026 B1 | 4/2003 | Dales et al. |
| 6,747,067 B2 | 6/2004 | Melnichuk et al. |
| 6,811,703 B2 | 11/2004 | Elliott |
| 6,841,085 B2 | 1/2005 | Werpy et al. |
| 6,923,838 B2 | 8/2005 | Maubert et al. |
| 6,994,827 B2 | 2/2006 | Safir et al. |
| 7,033,972 B2 | 4/2006 | Shikada et al. |
| 7,226,566 B2 | 6/2007 | Beierle |
| 7,458,999 B2 | 12/2008 | Schenck et al. |
| 7,846,979 B2 | 12/2010 | Rojey et al. |
| 7,888,540 B2 | 2/2011 | Deluga et al. |
| 2003/0119952 A1 | 6/2003 | Werpy et al. |
| 2004/0111968 A1 | 6/2004 | Day et al. |
| 2008/0006519 A1 | 1/2008 | Badger |
| 2008/0093209 A1 | 4/2008 | Noto |
| 2008/0216391 A1 | 9/2008 | Cortright et al. |
| 2008/0223269 A1 | 9/2008 | Paoluccio |
| 2008/0300435 A1 | 12/2008 | Cortright et al. |
| 2008/0317657 A1 | 12/2008 | Hall et al. |
| 2009/0007484 A1 | 1/2009 | Smith |
| 2009/0139139 A1 | 6/2009 | Tilman et al. |
| 2009/0151251 A1 | 6/2009 | Manzer et al. |
| 2009/0183430 A1 | 7/2009 | Schubert et al. |
| 2009/0217575 A1 | 9/2009 | Raman et al. |
| 2009/0253947 A1 | 10/2009 | Brandvold et al. |
| 2009/0308787 A1 | 12/2009 | O'Connor et al. |
| 2010/0040510 A1 | 2/2010 | Randhava et al. |
| 2010/0162780 A1* | 7/2010 | Scharf ............... 71/36 |
| 2010/0180805 A1 | 7/2010 | Cheiky |
| 2010/0218417 A1 | 9/2010 | Bauldreay et al. |
| 2010/0223839 A1 | 9/2010 | Perez et al. |
| 2010/0257775 A1 | 10/2010 | Cheiky |
| 2010/0270505 A1 | 10/2010 | Gallaspy et al. |
| 2010/0300866 A1 | 12/2010 | Van Aardt et al. |
| 2011/0023566 A1* | 2/2011 | Lodwig et al. ............ 71/14 |
| 2011/0177466 A1 | 7/2011 | Cheiky |

FOREIGN PATENT DOCUMENTS

| | | |
|---|---|---|
| WO | WO 2009004652 | 1/2009 |

OTHER PUBLICATIONS

R. Buerschaper, "Thermal & Electrical Conductivity of Graphite & Carbon at Low Temperatures," Jour. of App. Physics; (1994) pp. 452-454.

I.M. Lima, "Physiochemical & Adsorption Properties of Fast-Pyrolysis Bio-Chars & their Steam Activated Counterparts," J. Chem. Biotechnical (2010) 85, pp. 1515-1521.

Cheng, Chih-Hsin; "Stability of Black Carbon in Soils Across a Climatic Gradient," Jour. of Geophysical Research Biogeosciences; 113 (2008) G02027; pp. 1-10.

Lehmann, J.; Nutrient Avail. & Leaching in an Archaeological Anthrosol & Ferraisol of the Central Amazon Basin; Fertilizer, Manure,; Plant Soil 249 (2003); pp. 343-357.

Preston, C.M.; Black (Pyrogenic) Carbon: a Synthesis of Current Knowledge & Uncertainities w/Special Consideration of Boreal Regions; Biogeosciences 3 (2006); pp. 397-420.

Tryon, E.H.; "Effect of Charcoal on Certain Physical, Chemical, & Biological Properties of Forest Soils," Ecological Monographs, vol. 18, No. 1 (Jan. 1948); pp. 81-115.

Faludi, J.; "World Changing Change Your Thinking a Carbon-Negative Fuel;" Oct. 16, 2007; www.worldchanging.com.

Laird, David; "The Charcoal Vision: A Win Win Scenario," 2008, Agron, J., vol. 100, No. 1, pp. 178-181.

Ogawa; "Carbon Sequestration by Carbonization of Biomass & Forestation; 3 Case Studies," Mitigation & Adaption Strategies for Global Change, vol. 11 (2006); pp. 429-444.

Demirbas, "Effects of Temperature & Particle Size on Bio-Char Yield from Pyrolysis of Agricultural Residues," J. Anal, Pyrolysis, vol. 72 (2004); pp. 243-248.

Kim at al.; Characteristics of Crosslinked Potato Starch & Starch-Filled Linear , Low-Density Polyethylene Films Carbohydrate Polymers, vol. 50 (2002); pp. 331-337.

Norman, at al; "Best Management Practices for Reclaiming Surface Mines in Washington and Oregon," Open-File Report 0-92-2, revised ed. Dec. 1997; www.oregongeology.org Feb. 9, 2010.

E. Gegver & K. Hayek; "A Fully Programmable System for the Study of Catalytic Gas Reactions," 1985 J. Physc. E: Sci. Instrum. 18 836.

D.C. Elliott; "Liquid Fuels by Low-Severity Hydrotreating of Biocrude," Dev, in Thermochemical Biomass Conversion; vol. 1, pp. 611-621.

Dinesh Mohan, "Pyrolysis of Wood/Biomass for Bio-Oil; A Critical Review," Energy & Fuels (2006) 20, pp. 848-889 (1996).

Ramesh K. Sharma; "Catalytic Upgrading of Pyrolysis Oil," Energy & Fuels (1993), 7, pp. 306-314.

Thiam Leng Chew, "Catalytic Processes Towards the Production of Biofuels in a Palm Oil and Oil Palm Biomass-based Biorefinery," Bioresource Tech. 99 (2008), pp. 7911-8922.

K. Omata; "Optimization of Cu Oxide Catalyst for Methanol Synthesis under High C02 Partial Pressure Using Combinatorial Tools," App.Catalyst A: General 262 (2004), 207-214.

Kaoru Takeishi; "Dimethy Ether & Catalyst Development for Production of Syngas," Biofuels (2010) 1(1), pp. 217,226.

* cited by examiner

METHOD FOR ENHANCING SOIL GROWTH USING BIO-CHAR

CROSS-REFERENCE TO RELATED APPLICATIONS

This application is a divisional of, and claims the benefit of, U.S. patent application Ser. No. 13/154,213 filed Jun. 6, 2011, which is incorporated herein by reference in its entirety.

TECHNICAL FIELD

The present invention relates generally to methods for soil enhancement, and more particularly to methods for enhancing soil growth utilizing a high surface area, porous char.

DESCRIPTION OF THE RELATED ART

As the world continues to increase in population, severe strains are being placed on natural resources. One problem relates to growing a sufficient amount of food to feed an increasing world population. Agents that enhance soil growth are eagerly being sought to help in feeding this growing number of people. Charcoal is one such agent, but its use so far has been rather limited. Charcoal production has been known and practiced throughout the ages. Forest fires produce charcoal and this has been found at times to be beneficial to the soil. Combustion of wood in oxygen-depleted atmospheres produces charcoal, which retains nutrients but does not readily break down. Indeed, its mean residence time in soil has been estimated at millennia. See, Cheng, C. H., Lehmann, J, Thies, J E, and Burton, S. D. *Stability of black carbon in soils across a climatic gradient. Journal of Geophysical Research Biogeosciences* 113 (2008) G020227. Biochar can be an effective carbon sink and carbon sequestration agent as well as an agent for improving agricultural output.

Several investigations have shown that biochar added to soil can enhance soil growth under certain circumstances. For example, it has long been known that the Amazonian soil terra preta from Brazil consists of a mix of soil and charcoal that contains higher levels of plant nutrients than surrounding soils. The Amazon soil is anthropogenic soil, the charcoal resulting from the combustion of wood in kilns along with combustion of domestic and agricultural refuse. Regular kitchen refuse and ash are also deposited in the Amazon soil. Terra preta contains 9% biochar, whereas neighboring soils typically have a charcoal concentration of less than 0.5%. Soil fertility has persisted in excess of hundreds of years. However, it has been difficult to replicate this soil elsewhere. Biochar addition has been shown to increase the bioavailability of nutrients such as N and P. See, e.g., Lehmann J. DaSilva J P, Steiner C, Nehls T. Zech W. and Glaser W *Nutrient availability and leaching in an archaeological Anthrosol and a Ferralsol of the Central Amazon basin: fertilizer, manure and charcoal amendments. Plant Soil* 249 (2003) 343-357. See also, Tryon E H. *Effect of charcoal on certain physical, chemical, and biological properties of forest soils. Ecological Monographs* 18 (1948) 81-115. Under some circumstances, biochar has been shown to provide extra nutrients itself. Some farmers practice slash-and-char techniques in preference to more indiscriminate slash-and-burn soil management.

Previous attempts to incorporate high levels of biochar into soil have been ineffective in part because partial combustion leaves residual poly-aromatic hydrocarbons (PAHs) within the char. The PAHs are co-produced with the biochar and are adsorbed within the biochar. See, Preston, C. M. and Schmidt M. W. I. *Black (pyrogenic) carbon: A synthesis of current knowledge and uncertainties with special consideration of boreal regions. Biogeosciences* 3 (2006) 397-420. These hydrocarbons inhibit seed germination and repel microorganisms that are essential to soil growth such as fungi and bacteria. Although certain fungi are known to degrade PHAs in soils, it can take weeks for the degradation to start because the fungi are not able to colonize suitable environments. Approximately 80% of vascular plant families are colonized by arbuscular mycorrhizal (AM) fungi. These fungi are obligate symbionts and take up the plant's photosynthetic products in the form of hexoses while providing a high surface area network for the plant uptake of nutrients, especially phosphorus. Carbon produced from fossil fuels (e.g., coal, tar sands, petroleum) contains toxic compounds and it is not cost effective to remove or filter out these compounds. As a result, carbon from these sources is generally unsuitable for soil addition.

US Patent Publication No. 2010/0040510 discloses a multistage pressurized fluidized bed gasifier operating between 780° C. and 1100° C. that converts biomass to syngas and biochar. The biochar is said to be capable of being added to soil. US Patent Publication No. 2008/0317657 provides a system and method for sequestering carbon in the form of char added to soil; the char is created by gasifying biomass in an unspecified reactor vessel. A low heating value producer gas is a by-product of the process. US Patent Publication No. 2004/0111968 discloses pyrolyzing biomass in an unspecified reactor to produce char and pyrolysis gases, which are steam reformed to hydrogen. The char is treated with unspecified nutrients to become a carbon based fertilizer. US Patent Publication No. 2010/0300866 details a method for converting pyrolyzable organic matter to biocarbon involving the recirculation of collected volatile vapors.

U.S. Pat. No. 6,811,703 teaches using a solid phase mixed solvent polymer as a soil amendment for removing and retaining solvated organic compounds and inorganic ions from water sources, as well as adhesively coating the polymer onto sand along with at least one ion exchange material. The solid phase mixed solvent polymer is said to improve organic leachate adsorption, and better retention of nutrients in the soil by providing additional ion exchange network for the soil. The ion exchange is said to be a favorable mechanism for fertilizer ion retention within the exchanger, followed by a slow release to the roots. Clays have also been added to enhance soil growth. A problem with this approach is that upon exposure to water, the clay swells and soil pores become clogged.

BRIEF SUMMARY OF EMBODIMENTS OF THE INVENTION

The above methods of modifying biochar to enhance soil growth differ substantially from the methods set forth in the following embodiments of the invention. These embodiments utilize a novel type of char (referred as BMF char) that is generated according principles delineated in co-owned, co-pending U.S. patent application Ser. No. 13/103,905, titled "Method for Biomass Fractioning by Enhancing Thermal Conductivity," the content of which is incorporated herein by reference in its entirety. This patent application teaches systems and method for generating BMF char using a biomass fractioning reactor in which biomass is fractioned into thin sheets that are subjected to specific temperature ramps and pressure shocks.

Embodiments of the present invention disclose a novel process for rendering the BMF char suitable as a soil growth agent. This process may comprise several steps including: (i)

creating the BMF char, (ii) expelling detrimental agents within the BMF char, (iii) rendering the internal surface area of the BMF char hydrophilic, and (iv) adding suitable nutrients and microorganisms to the BMF char. In addition to acting as a soil enhancing agent, the BMF char can sequester carbon for long periods of time. An alternate method for carbon sequestration via coal production from biomass is disclosed in co-owned, co-pending US Patent Publication No. 2010/0257775, titled "System and Method for Atmospheric Carbon Sequestration," the content of which is incorporated herein by reference in its entirety.

Some embodiments of the present invention involve an agent for enhancing soil growth that utilizes a novel char derived from a biomass fractioning system.

Further embodiments of the present invention involve a method for processing BMF char to be readily serviceable for soil amendment.

Additional embodiments of the present invention involve a method for sequestering carbon for long periods of time.

A particular embodiment of the invention is directed toward a method for the production of an agent for enhancing soil growth, comprising: (i) grinding a biomass feedstock to produce ground biomass particles; (ii) subjecting the ground biomass particles to sequential or concurrent ramps of temperature and pressure shocks; (iii) selectively collecting at least one volatile component as it is released from the ground biomass particles; (iv) collecting a last remaining nonvolatile component comprising BMF char; (v) rendering a surface of the BMF char hydrophilic; (vi) exposing the BMF char to microorganisms; and (vii) adding the BMF char to soil.

According to some implementations, the biomass particles are ground to a diameter between about 0.001 inch and about 1 inch. The method may further comprise dispensing the ground biomass particles into thin sheets whose total thickness is a multiple of the ground biomass particle diameter before subjecting the ground biomass particles to sequential or concurrent ramps of temperature and pressure shocks. In some case, the multiple may be any real number in the range of 1 to 30. The biomass feedstock can be used to produce different BMF chars based on a composition of the biomass feedstock. Pressure shocks may vary in magnitude from 0.2 MPa to 10 GPa, and an admixture of pressure shocks of differing magnitudes can be combined with pressure shocks applied over a range of times.

In some embodiments, the temperature ramp includes a sufficiently high temperature to create a nonvolatile carbonaceous material within the ground biomass particles. In addition, the pressure shocks can increase thermal conductivity of formed nonvolatile carbonaceous material within the ground biomass particles. The pressure shocks may also decrease the effective density of the ground biomass particles. In some cases, the temperature ramps and pressure shocks are conducted in an atmosphere containing a supercritical fluid. In further embodiments of the invention, a pH of the BMF char can be controlled via pH adjustment agents. In various embodiments, the BMF char may be activated and a pH of the soil modified to accept the addition of BMF char.

According some implementations of the above method, the surface of the BMF char is rendered hydrophilic by removing adsorbed gas within char pores, wherein the surface of the BMF char is rendered hydrophilic by high temperature removal of adsorbed hydrocarbons. In some embodiments, adsorbed gases are removed by water infiltration, vacuum suction, ultrasonic means, or impact means. In other embodiments, adsorbed gases are removed by introducing a water solution containing soluble plant nutrients. According to various embodiments of the invention, microorganisms can include members of at least one of fungi, bacteria or archaea. In some cases, fungi are selected from members of the phyla Glomeromycota and the BMF char contains glomalin structures.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

FIG. 2a is a flow diagram illustrating the generation of BMF char from biomass, including an optional activation step, whereas

FIG. 5a is an SEM image of BMF char from corn, while

FIG. 6a is a diagram illustrating growth of lettuce plants in soils containing different concentrations of char treated according to a method of the present invention, whereas

FIG. 7a is an SEM image of BMF char, while

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

Embodiments of the invention are directed toward methods for enhancing soil growth utilizing a high surface area, porous char. In some embodiments, the char is made using a method that modifies biomass to have a hydrophilic surface and to exhibit a hospitable environment for bacteria, archaea and fungi necessary for plant growth.

Figure 1:
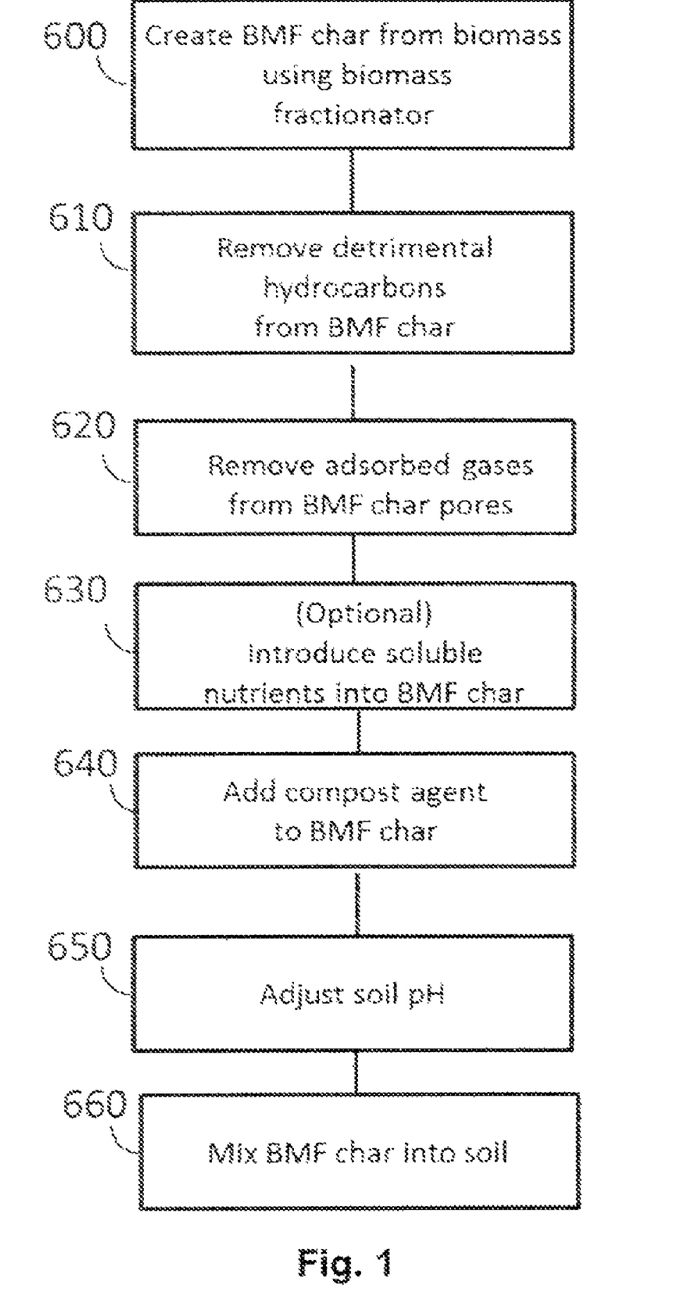
FIG. 1 is a flow diagram depicting a process for rendering biochar suitable as a soil enhancing agent, in accordance with an embodiment of the invention.

FIG. 1 illustrates the basic steps for the creation of a novel biochar that is modified to act as a soil growth enhancement agent, in accordance with an embodiment of the invention. The initial step comprises a BMF char generation process 600 in which BMF char is created from biomass, for example using a biomass fractionator. The subsequent steps involve a process 610 for removal of detrimental hydrocarbons from the BMF char, a process 620 for removal of adsorbed gases from the BMF char, an optional process 630 for introducing soluble nutrients into the BMF char, a process 640 for adding a compost agent to the BMF char, a process 650 for adjustment of soil or BMF char pH, and a process 660 for mixing the BMF char with soil. The full nature of the invention will become evident from the following description of each step.

Bio-Char Generation

Figure 2A:
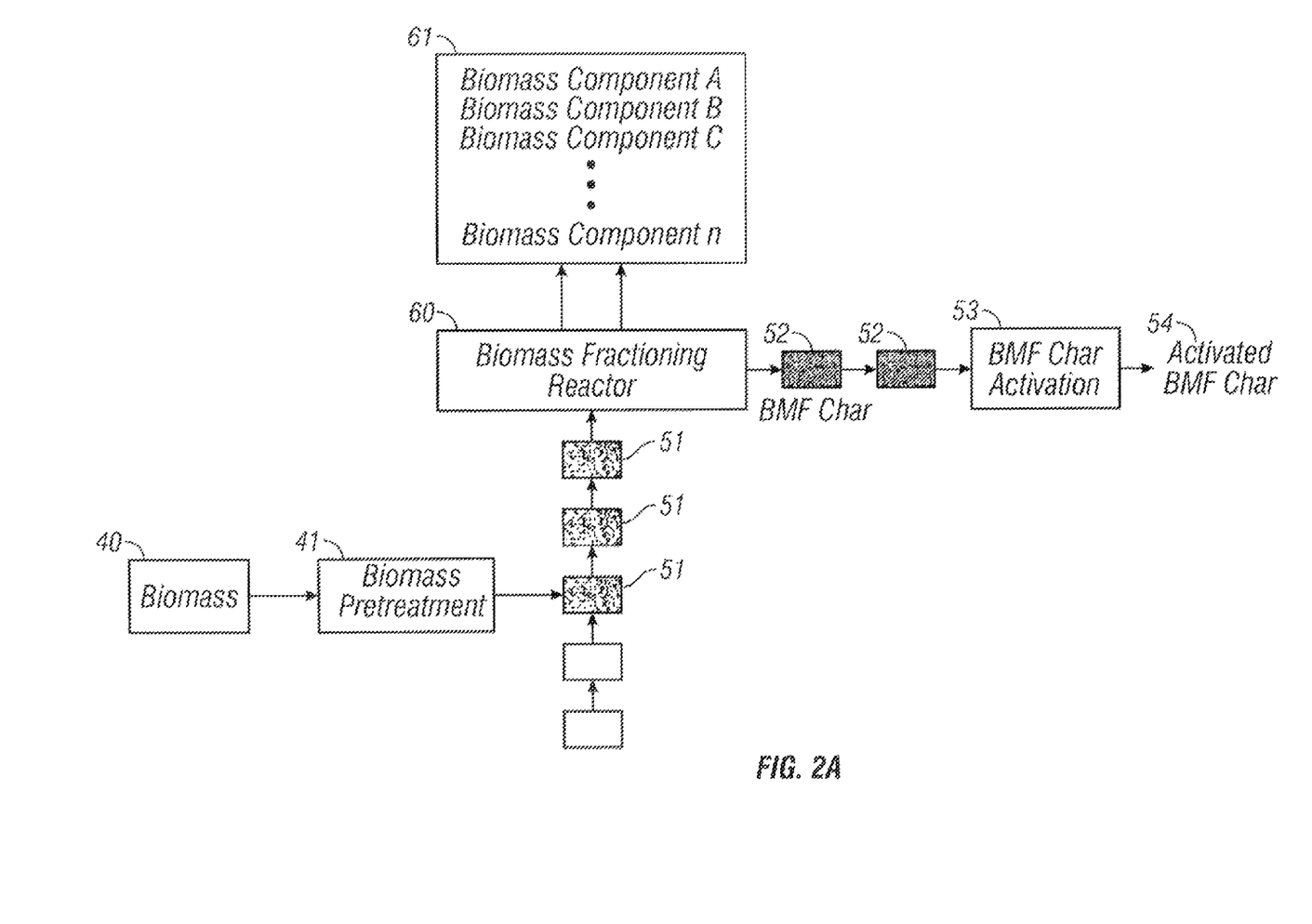

The basic principles behind bio-char generation (process 600) are disclosed in co-owned, co-pending U.S. patent application Ser. No. 13/103,905 entitled "Method for Biomass Fractioning by Enhancing Thermal Conductivity," the content of which is incorporated herein by reference in its entirety. The following is a possible embodiment for bio-char generation. Referring now to FIG. 2a, biomass 40 is optionally pretreated in process 41 and loaded piecemeal onto a plurality of movable biomass reaction chambers 51 movable by common drive mechanisms such as gear drives, chain drives, ratcheting sprockets, etc. The reaction chambers 51 may be arranged on a disc that can rotate continuously or in a stepwise fashion. The pretreatment may comprise a drying step or other steps.

As used herein, the term 'biomass' includes any material derived or readily obtained from plant sources. Such material can include without limitation: (i) plant products such as bark, leaves, tree branches, tree stumps, hardwood chips, softwood chips, grape pumice, sugarcane bagasse, switchgrass; and (ii) pellet material such as grass, wood and hay pellets, crop products such as corn, wheat and kenaf. This term may also include seeds such as vegetable seeds, sunflower seeds, fruit seeds, and legume seeds. The term 'biomass' can also include: (i) waste products including animal manure such as poultry derived waste; (ii) commercial or recycled material including plastic, paper, paper pulp, cardboard, sawdust, timber residue, wood shavings and cloth; (iii) municipal waste including sewage waste; (iv) agricultural waste such as coconut shells, pecan shells, almond shells, coffee grounds; and (v) agricultural feed products such as rice straw, wheat straw, rice hulls, corn stover, corn straw, and corn cobs.

With further reference to FIG. 2a, the biomass 40 may be ground by a variety of techniques into a particle size suitable for dispensation into the reaction chamber 51. Particle size may range from 0.001 inch to 1 inch in diameter, limited by processing equipment size and thermal transfer rates.

Embodiments of the invention feature a biomass chamber 51 that is much wider and longer than it is thick. In some cases, biomass is dispensed into thin sheets whose total thickness is 1 to 30 times the biomass particle size. A preferred thickness for the chamber for uncompressed biomass (which is ground or chopped to ⅛" or smaller) is approximately ¾" in thickness. As the biomass is heated and further pulverized (as discussed below), the emerging BMF char 52 quickly condenses to a layer about ¹⁄₁₀" thick. This aspect ratio ensures mild pyrolyzing conditions that allow the collection of useful chemical compounds known as bio-intermediary compounds as well as the production of BMF char 52. A person of skill in the art will appreciate that these biomass chambers 51 can be sized in width and length along with the diameter of their corresponding drive disc to any such size as appropriate for the desired throughput for the biomass fractionator, without departing from the scope if the invention.

Figure 2B:
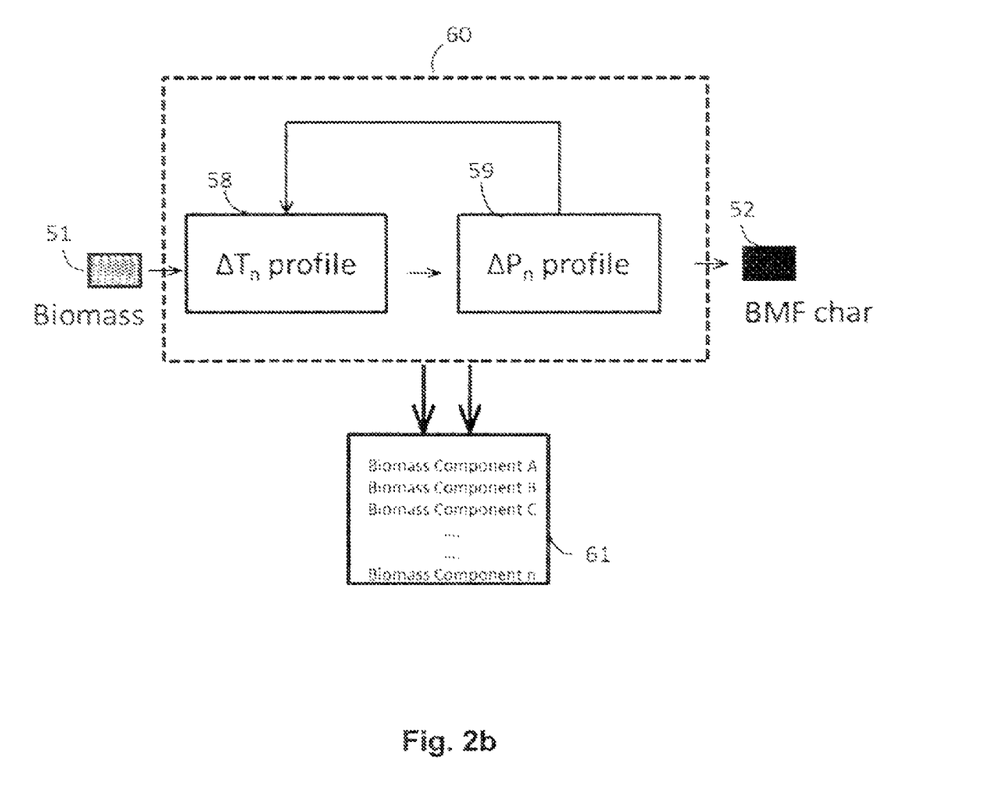
FIG. 2b is a flow diagram illustrating the basic operational principles behind the conversion of biomass into BMF char, in accordance with an embodiment of the invention.

Referring to FIG. 2b, the ground biomass is subjected first to a heating profile $\Delta T1$, typically a linear temperature ramp, by a heating agent such as a metal anvil at processing station 58. In some cases, the purpose of this first $\Delta T1$ profile is to dewater the biomass. Subsequent $\Delta Tn$ profiles end at progressively higher temperatures and have the purpose of outgassing and thermochemically converting biomass into useful bio-compounds with progressively higher devolatilization temperatures. In order to accomplish this devolatilization in a selective manner, the temperature treatment is accompanied by a pressure treatment. Compacting station 59 (e.g., comprising a series of anvils) subjects the biomass to accompanying pressure profiles, $\Delta Pn$, which comprise a sequence of pressure shocks that exploit the inherent compressional features of carbon.

In some embodiments, the temperature profiles are linear ramps ranging from 0.001° C./sec to 1000° C./sec, and preferably from 1° C./sec to 100° C./sec. By way of example, processing heating station 58 may be heated by electrical heating elements, direct flame combustion, or by directed jets of heated working gas or supercritical fluid. The heating profile and the pressure compaction profile may be linked via a feedback loop and may be applied by the same agent simultaneously. Compacting station 59 may be controlled by electrically driven devices, air compressed devices, or any other form of energy that serves to impact load the biomass. BMF char 52 remains after these processing steps. It may then be optionally activated by reacting it via process 53 with oxygen, methane, carbon dioxide or steam at high temperatures to create an ultra high surface area porous material 54.

Figure 3:
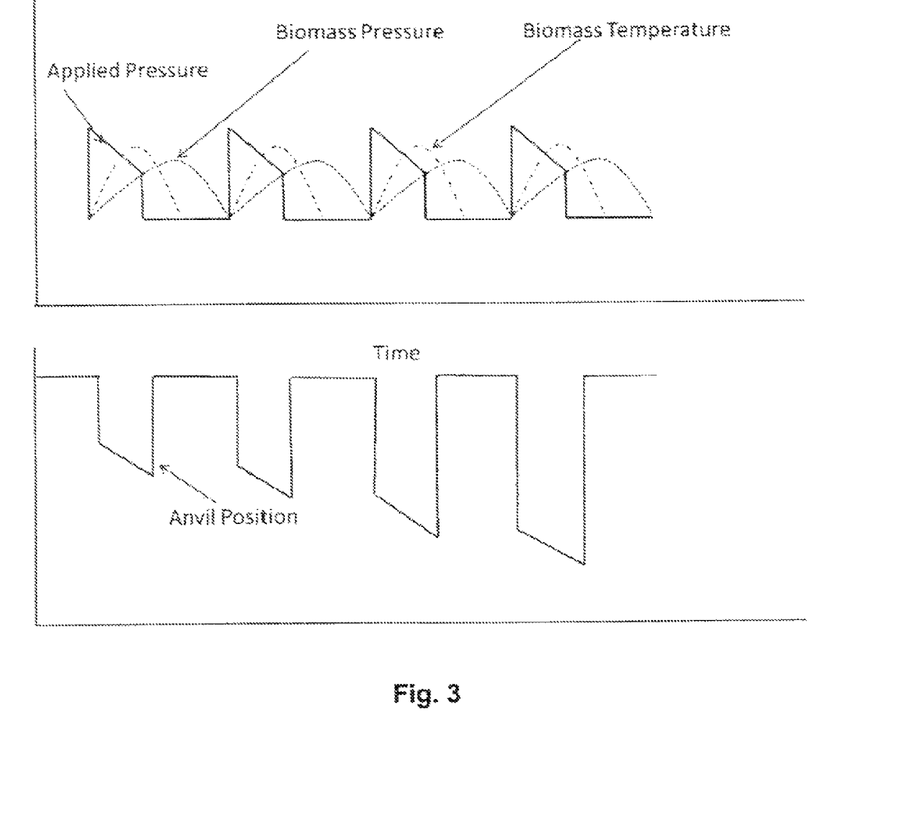
FIG. 3 is a diagram illustrating an example of applied pressure and corresponding biomass pressure and temperature within the reaction chamber, as well as anvil position during this time interval, in accordance with an embodiment of the invention.

The selective pyrolysis of the biomass 40 arises out of the interplay between the applied pressure pulses, applied temperature and resultant pressures and temperatures experienced by the biomass. The process is illustrated diagrammatically in FIG. 3, which shows applied pressure, biomass temperature, biomass pressure and anvil position as a function of time. It is understood that a wide variety of different types of pressure pulses may be applied, and that the entire illustration is a pedagogic device. In FIG. 3, pressure shocks applied via compacting station 59 are shown as a series of triangular pressure pulses with an unspecified rest time. The process starts out by utilizing the thermal conductivity of water. The biomass is first subjected to a temperature ramp sufficient to cause the biomass to release water. The released heated water vapor is then subjected to a pressure shock which compresses the steam, thus accelerating the biomass decomposition. It may be possible for the steam to attain supercritical form, though that is not a requirement for the present invention.

A short time after peak pressure is applied, the anvil is pushed back by the pressure of extracted volatile compounds. When the volatile compounds are removed along with the steam, pressure within the biomass is decreased suddenly. Biomass temperature rapidly returns to base levels, and the anvil returns to its un-extended base position. After the water has been removed entirely from the biomass, the applied temperature causes hot localized areas within the biomass which initiate carbon formation. In turn, compressive impacts on the newly formed carbon increase the thermal conductivity of the carbon. The increased thermal conductivity serves to efficiently transmit heat energy needed to break down the biomass to the next stage in its decomposition. Furthermore, because carbon exhibits compressional memory, compressive impacts are sufficient to exert this effect on thermal conductivity.

The compressional memory of carbon has been indirectly demonstrated in studies of commercial carbon resistors as low pressure gauges. See Rosenberg, Z et al *International Journal of Impact Engineering* 34 (2007) 732-742. In these studies, metal discs were launched from a gas gun at high velocity and impacted an epoxy or Plexiglas target in which a carbon resistor is embedded. Resistance changes were measured as a function of time after impact. It was noted that the resistance decreased rather rapidly in less than a microsecond, and stayed low for several microseconds, in some cases over 10 microseconds, until it began to increase gradually to pre-impact levels. There is essentially a memory effect or a slow relaxation after the impact. As electrical resistance and thermal conductivity are inversely correlated for carbon as for metals (See, for example, Buerschaper, R. A. in *Journal of Applied Physics* 15 (1944) 452-454 and *Encyclopedia of Chemical Technology, 5th edition*), these studies reveal a compression memory on the part of the carbon. This compression memory is at least partly utilized in embodiments of the invention.

Embodiments of the invention also utilize the increase in thermal conductivity as carbon is compressed. The change in electrical resistance with pressure in carbon microphones is a well-known effect utilized by carbon telephones and carbon amplifiers. U.S. Pat. No. 203,016, U.S. Pat. No. 222,390 and U.S. Pat. No. 474,230 to Thomas Edison, describe apparatus that transform sound compressions (vibrations) to changes in electrical resistance of carbon granules. Carbon is even more sensitive than most metals in its inverse relationship between electrical resistance and thermal conductivity. Below are data indicating the thermal conductivity of various substances (CRC Handbook of Chemistry and Physics, 87th edition) in comparison to the measured thermal conductivity of BMF char:

TABLE 1

Select Thermal Conductivities in W/(m · K)

| Material | Thermal Conductivity |
|---|---|
| Copper | 390 |
| Stainless Steel | 20 |
| Water | 0.6 |
| Dry Wood | 0.3 |
| Fuels | 0.1 to 0.2 |
| Carrier Gases ($H_2$, $N_2$, etc.) | 0.01 to 0.02 |
| Carbon Char | 0.01 to 0.05 |
| BMF char | 1 to 5 |

As the thermal conductivity of the formed carbon within the biomass increases due to pressure shocks, it becomes consequently easier to attain mild pyrolysis conditions within the biomass. As higher temperatures are reached, the fact that carbon is a better heat transfer agent than water enables higher boiling compounds to become volatile. Pressure shocks serve to compress these higher boiling compounds and contribute to fracturing cell walls within the biomass. The process is illustrated by FIG. 3 which shows anvil extension at peak pressure getting longer with subsequent pulse application, thus indicating successive biomass pulverization in conjunction with release of useful higher boiling compounds.

A variety of pressure profiles $\Delta Pn$ are effective in increasing the carbon thermal conductivity. The magnitude of the pressure can vary from 0.2 MPa to 10 GPa and may be applied via a number of different technologies, including air driven pistons, hydraulically driven pistons, and explosive driven devices. The duration of the pressure application can vary from 1 microsecond to 1 week. It is understood that pressure pulses of different magnitudes and different time durations may be admixed to yield optimum results.

The efficient heat energy transfer executed by embodiments of the present invention can be enhanced by the addition of supercritical fluids in the reaction chamber. It is known that supercritical fluids can improve heat transfer as well as accelerate reaction rates. Certain embodiments can operate with supercritical carbon dioxide, supercritical water, supercritical methane, supercritical methanol, or mixtures of the above. It is possible that supercritical conditions are created internally with some pressure and temperature profiles.

BMF char 52 remains after these processing steps. The physical characteristics of the char will differ depending on the starting biomass material, which can include any of the above-identified materials such as wood, grasses, municipal solid waste, etc. Different biomass feedstocks are expected to produce different types of BMF chars, varying in porosity and other physical characteristics. The biomass feedstocks can be fed individually or as mixtures of different feedstocks to produce chars containing different physical characteristics.

After the BMF char is formed, a last processing step is to transfer the BMF char out of the reaction chamber for a subsequent storage or filling into a bio-char reactor for subsequent optional activation 53. The transfer may be accomplished via any number of mechanical means, including a press bar outfitted with a scraping knife.

Figure 4:
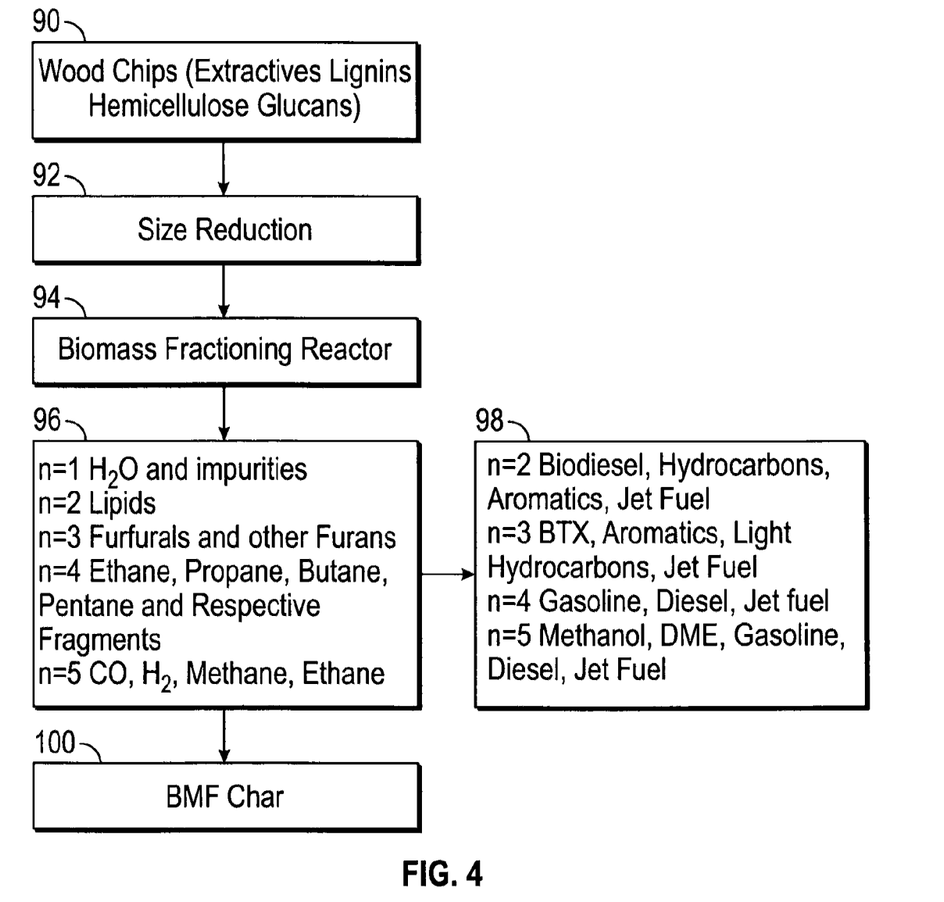
FIG. 4 is a flowchart illustrating an embodiment of the stepwise decomposition of biomass and accompanying formation of BMF char, in accordance with an embodiment of the invention.

FIG. 4 illustrates an embodiment of the stepwise decomposition of biomass and accompanying formation of BMF char using the principles outlined above. Referring to FIG. 4., dried biomass 90 is provided in the form of wood chips containing extractives, lignins, hemicellulose, and glucans. Operation 92 involves a size reduction wherein the biomass is ground to 1/16" size and placed on rotating pallets in a chamber approximately 3/4" thick. Within the biomass fractioning reactor 94, the biomass is subjected to a temperature ramp of 25° C./sec in an oxygen-free atmosphere for varying amounts of time with intermittent pressure shocks of 80 MPa lasting for 2 seconds with a 50% duty cycle. The following distribution 96 of devolatilized compounds was observed:

TABLE 2

Distribution of Devolatilized Compounds

| Stage | Volatile Compound | Char Formed | Fractionator Temperature |
|---|---|---|---|
| n = 1 | $H_2O$ and $H_2O$ soluble impurities | | 100-150° C. |
| n = 2 | Lipids | BMF Char (2) | 150-250° C. |
| n = 3 | Furfurals and other furans | BMF Char (3) | 250-375° C. |
| n = 4 | Ethane, Propane, Butane, Pentane and respective fragments | BMF Char (4) | 375-00° C. |
| n = 5 | CO, $H_2$, Methane, Ethane | BMF Char (5) | >500° C. |

In addition to showing devolatilized components, FIG. 4 also shows the resultant BMF char 100 and possible catalytic conversion of devolatilized organic components to various liquid fuels 98 such a biodiesel, hydrocarbons, aromatics, jet fuel, BTX, light hydrocarbons, gasoline, diesel, methanol, and DME. The organic chemicals 96 can also be useful on their own as co-produced chemicals. By contrast, typical pyrolysis processes do no exhibit a clear volatilization profile as shown above.

BMF Char Activation

The BMF char is preferably activated prior to use. Activation is a well-known procedure for increasing char surface area and adsorptive capabilities. See, for example, Lima, I. M. et al, in *Journal of Chemical Technology and Biotechnology*, vol. 85, (2010), pp. 1515-1521. The activation step is an optional pretreatment and selective combustion step which aims to create additional surface area to accelerate subsequent desired reactions. Typical activating agents include $CO_2$, $H_2O$ and $O_2$. Table 2 shows data acquired using different activation agents at 900° C. for BMF char generated using a biomass fractioning reactor. In the case, the BMF char was derived from corn cobs.

The increased surface area of the BMF char upon activation comes at the expense of a loss of material, which serves to create a porous structure within the char. Whether exposed to oxygen or methane and air, a loss of approximately 40% of the initial weight was measured. Activation procedures can produce surface areas in excess of 500 m2/g.

TABLE 3

Effect of Activating Agent on BMF Char

| Char Source | Activation Agent | Activation Time | Activation Temp ° C. | BMF Char Loaded, g | Activated BMF Char, g |
|---|---|---|---|---|---|
| Corn Cobs | $O_2$ | 3 Hours | 900 | 47.5 | 29 |
| Corn Cobs | $CH_4$, air | 3 Hours | 900 | 46 | 29.5 |

Figure 5A:
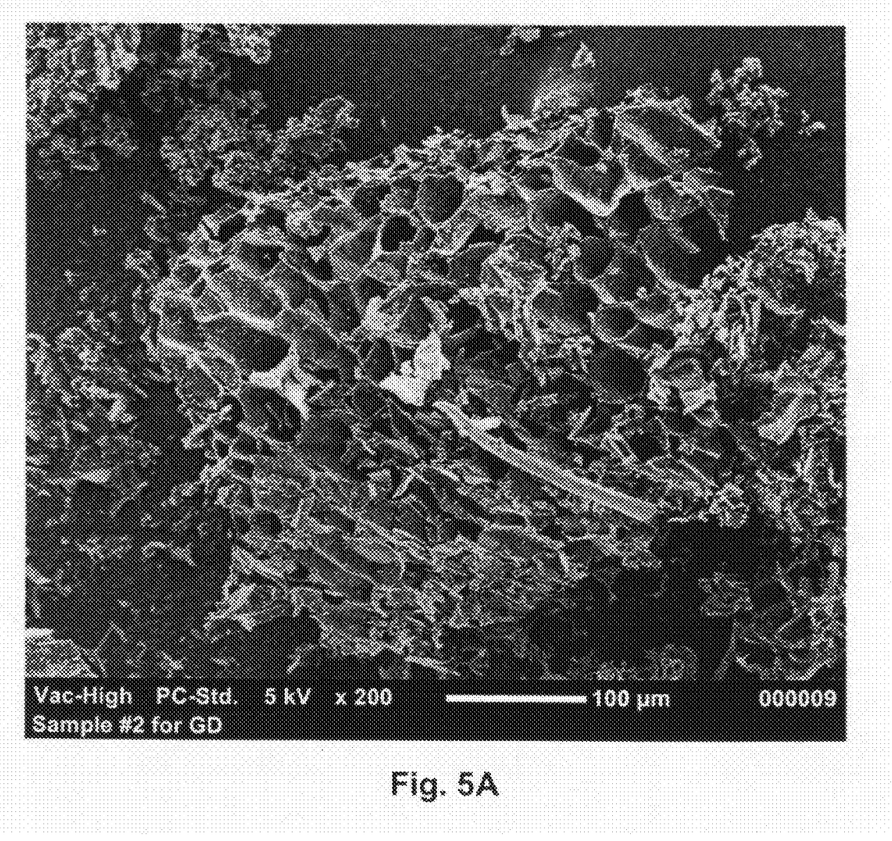
Figure 5B:
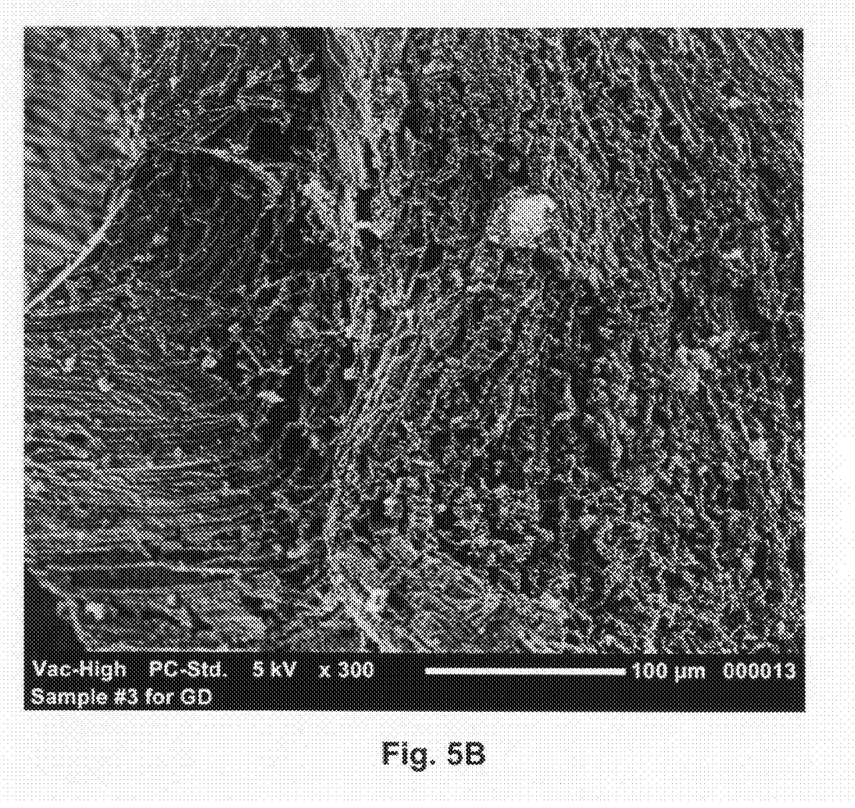
FIG. 5b is an SEM image of char from corn activated with steam.

An SEM micrograph of unactivated BMF char derived from corn cobs is depicted in FIG. 5a, while FIG. 5b is an SEM micrograph of corn cobs char after steam activation at 900° C. This material had a measured BET surface area of 760 m2/g and an average pore size of 45 Å, whereas unactivated material typically yields BET surface areas below 100 m2/g.

Due to a different processing history, the BMF char arising out of this biomass fractioning process is different from carbonaceous deposits formed from pyrolyzers or coke from petroleum plants. A system capable of embodying the method of the present invention is described in co-owned, co-pending U.S. Patent Application No. 2010/0180805 entitled "System and Method for Biomass Fractioning," the content of which is incorporated herein by reference in its entirety. This system comprises a biomass load and dump station, a heated pulverizing processing station for compressing the biomass, a biochar dumping station for removing residual biochar and a plurality of biomass reaction compartments able to carry the biomass from station to station.

Removal of Hydrocarbons

Typical charcoal contains a variety of hydrocarbons in various stages of decomposition, depending on the last temperature to which the charcoal was subjected. In a typical carbonization of wood, different stages of volatilization are reached depending on the temperature. During the early stages of heating, wood releases water vapor as it absorbs heat. Wood decomposition starts above 110° C., yielding primarily CO, $CO_2$, acetic acid, methanol and minor traces of other components. Exothermic decomposition starts around 280° C. and tar starts to form. Just above 400° C., the wood has been essentially converted into charcoal, but this charcoal still contains about ⅓ of its weight in tar material. Further heating is needed to drive off the tar. Because of the highly porous nature of wood, it is difficult to remove tar unless sufficiently high temperatures are reached beyond the equilibrium decomposition temperature of tar components.

The methods described herein differ substantially from typical carbonization in that mild pyrolysis is used to obtain a variety of useful volatile compounds, thus minimizing tar formation. The resultant BMF char is substantially different from typical charcoal in morphology and residue. Small amounts of hydrophobic hydrocarbons, in particular polyaromatic hydrocarbons (PAHs), can inhibit colonization of the BMF char by microorganisms. The first step in rendering the BMF char hospitable for subsequent microorganism invasion is to expel these hydrophobic hydrocarbons. Temperatures above 700° C. are required to remove the hydrophobic hydrocarbons from the BMF char walls. The hydrocarbon removal step may be combined with the activation step.

Removal of Adsorbed Gases from Char Pores

The next step in rendering the BMF char more hydrophilic involves removing adsorbed gases within the BMF char pores to allow water infiltration. This is important because the BMF char can be a high surface area compound (typically in excess of 300 m2/g in activated form) which contains significant amounts of strongly adsorbed gases within its pores. These gases are strongly adsorbed on pore surfaces and removal is highly beneficial. A simple method for removal of adsorbed gases is to immerse the BMF char in boiling water. This may be referred to herein as the "wetting step."

Optional soluble nutrients may be introduced during or after the wetting step. The nutrients enter into a high surface area porous environment and can exchange with adsorbed gases to some degree. Nutrients can include macronutrients containing nitrogen, phosphorus, potassium, calcium, magnesium, and sulfur as well as micronutrients containing molybdenum, zinc, boron, cobalt, copper, iron, manganese and chloride. The high surface area, porous BMF char affords plants access to relatively significant amounts of nutrients. Additionally, the BMF char retains these nutrients at times when rainfall tends to wash them off from the soil in the absence of BMF char. Besides water infiltration, other methods include ultrasonic, vacuum and impact removal of air.

Addition of Beneficial Microorganisms

Once wetted, the BMF char is ready to accept beneficial microorganisms. These microorganisms may comprise fungi, archaea and bacteria, which supply nutrients to plants symbiotically. The microorganisms may be introduced in a number of different ways, including mixing the BMF char with compost and water, adding compost tea to the BMF char, blending the latter with compost, or blending the BMF char with potting soil. In embodiments using a compost tea, the product may be purchased at suppliers such as Bu's Brew Biodynamic Tea® (Malibu Compost Inc, Santa Monica, Calif.), Nature's Solution. Compost Tea® (Nature's Technologies International LLC, Novato, Calif.) or MycoGrow® (Fungi Perfecti, Inc., Olympia, Wash.). The compost tea may be agitated to maintain an optimum oxygen concentration for microorganisms to thrive. Electric bubbling aerators, porous stones, or manual stirring are suitable methods to maintain sufficient aeration. Different compositions of fungi, archaea and bacteria may be used, depending on target soil.

A particularly beneficial fungi is the arbuscular mycorrhizal fungi, which expresses the glycoprotein glomalin on their hyphae and spores. These fungi are members of the phyla Glomeromycota. This protein helps to bind soil particles together and is responsible for good soil tilth. When introduced into biochar, the fungi will express glomalin within the biochar pores and aid in maintaining good soil structure by binding the biochar to soil particles. Additionally, the root structure provided by the hyphae allows nutrients to penetrate in and out of the high surface area environment provided by the biochar.

Adjustment of soil pH

It has been long been recognized that soil pH is an important variable in maintaining soil health and productivity. Soil pH tends to modify the bioavailability of plant nutrients.

Some soils are inherently acidic or basic in nature and a soil amendment needs to consider its effect on soil acidity. Biochar can differ in its effect on soil pH depending on the biomass source of the biochar. By way of example, the decomposition of corn cobs leaves significant amounts of $K_2O$ in the biochar residue, which tends to render the biochar basic. Addition of this basic biochar to a soil that is already basic is detrimental to the soil. pH management has been practiced inadvertently by Amazon Indians in creating terra preta soils. Other materials are always present with charcoal in terra preta soils, such as bones, fired clay bits and wood ash. These materials buffer the acidic Latrelite soils. The bones and wood ash balance the pH of the acidic clay soils.

Soil pH can be managed in several ways, including: (i) shifting soil pH by adding pH adjusting compounds directly to the soil after BMF char addition; (ii) adding additives to the BMF char that can shift the BMF char pH; and (iii) adding BMF char directly to the soil and allowing it to self-neutralize for extended periods of time.

The first approach utilizes well known pH adjustment reactants applied to soil. Neutralization compounds useful for acidic biochar can include anions selected from the group of: bicarbonates, carbonates, hydroxides, amines, nitrates, halides, sulfonates, phosphates, and carboxylates. These compounds may comprise one or more functional groups within a polymer, as well as oxides such as calcium oxide and magnesium oxide, which produce basic compounds upon exposure to air. Neutralization compounds useful for basic biochar can include inorganic acids such as HCl, $H_3PO_4$, and $H_2SO_4$, and organic acids such as humic, vanillic and ferulic acids. A dispersant may be optionally used.

Regarding the second approach, any of the compounds listed in the first approach may be applied directly to the BMF char. Additionally, BMF char may be made less alkaline by impregnating it with bacterial compost tea (vide infra) containing acidic ingredients such as molasses, plant juice, or algal extractives. The biochar may be made more alkaline by addition of alkaline agents such as lime, bones, potassium carbonate or potassium hydroxide. Buffering agents may also be added. The third approach requires mere long term exposure to the atmosphere to neutralize via carbonic acid formation.

Mixing Soil and Biochar

A wide variety of different techniques exist for applying the BMF char to soil. The incorporation of BMF char into soil may be accomplished via BMF char integration into traditional farm machinery, such as the use of manure or lime spreaders in conjunction with plowing methods utilizing rotary hoes, disc harrows, chisels, etc. Banding methods which allow BMF char use without significantly disturbing the underlying soil may also be used. The BMF char may be mixed in solid form along with manure, compost or lime, or mixed with water or liquid manure and applied as a slurry. It may also be mixed with topsoil or applied directly to an area where tree roots will extend.

Illustrative Example 1

Effect of Char Concentration

Figure 6A:
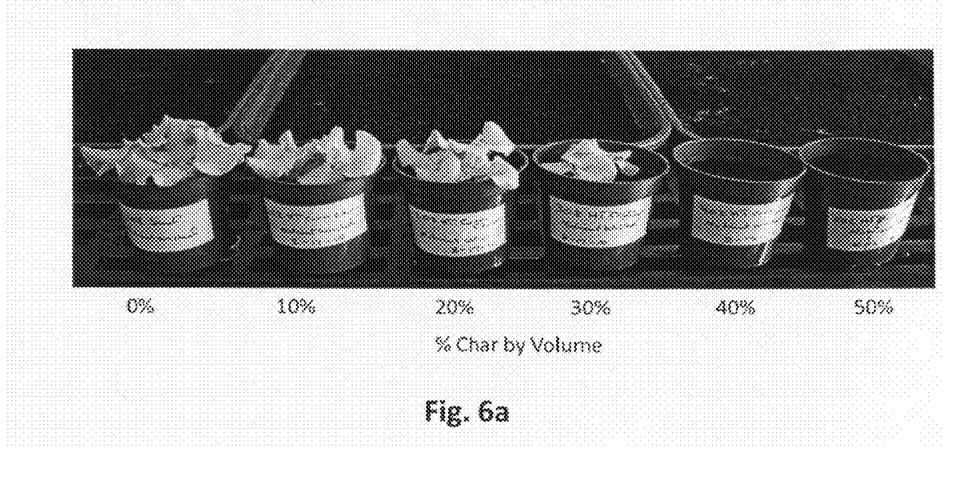

FIG. 6a shows plantings of Black Seed Simpson lettuce in soils containing different concentrations of steam activated corn char made hydrophilic via the above-described methods. The corn char had a BET surface area of 760 m2/g (depicted in FIG. 5b). The data shown is 8 days after planting. Char pH was adjusted to 8.2 via seltzer water. From left to right, FIG. 6a shows data from lettuce grown in soils containing 100% sand, 10% char and 90% sand, 20% char and 80% sand, 30% char and 70% sand and 40% char and 60% sand (by volume). The char was washed with Dyna-Grow® nutrients prior to use. It is shown in this case that soils containing even 30% char allow lettuce growth; however, inhibition of soil growth is evident for the 40% and the 50% char soils Illustrative Example 2

Effect of Nutrient Washing

Figure 6B:
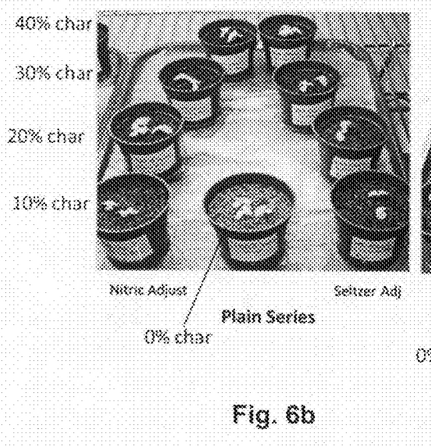
FIG. 6b-6c are images depicting growth of plants in pH-adjusted soils and nutrient-washed soil containing varying amounts of woodchar and sand.
Figure 6C:
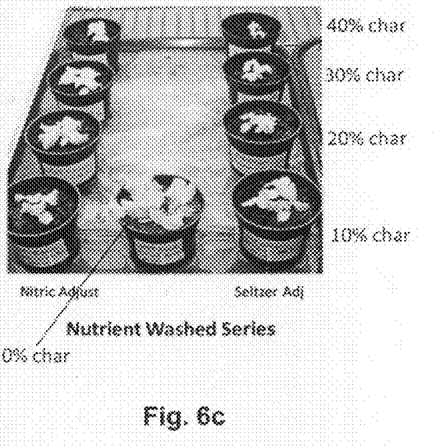

FIGS. 6b and 6c demonstrate the effect of nutrient addition on the growth of Black Seed Simpson lettuce plants grown in soils containing different char concentrations. The char was derived from unactivated wood chip made hydrophilic via hydrocarbon expulsion and removal of adsorbed gases. The char exhibited a pH around 9 when wet. In particular, FIG. 6b shows nine plantings, all containing no external nutrient addition. The first row shows experiments with soil containing 10% char and 90% sand by volume, except for the potting in the middle which contains 100% sand. All the pottings on the left were subjected to a pH adjustment by nitric acid, adjusting the pH close to neutral. All the pottings on the right were subjected to a pH adjustment by buffered seltzer bringing the pH to around 8. The second row shows two pottings, both containing soil comprised of 20% char and 80% sand by volume. The third row shows pottings with 30% char and 70% sand, and the fourth shows potting with 40% char and 60% sand. It is evident that plant growth is occurring even for soils containing the highest concentration of char, and that this growth is similar for both types of adjustments. FIG. 6c demonstrates similarly treated soils and pH adjustments, except for the addition of commercially available plant nutrients for all samples. It is observed that soil growth again occurs for all soil compositions, and that the growth is enhanced due to the addition of nutrients.

Illustrative Example 3

Introduction of Microorganisms into Biochar

In a two-gallon plastic container, 5 liters of distilled water are poured and aerated with an electric motor for 1 hour in the presence of a porous stone. 6 ml of molasses (Grandma's Molasses®, B&G Foods, Inc.) are then added along with 4 grams compost ingredient (Mycrogrow®, Fungi Perfecti Inc.) containing the following mixture of fungi and bacteria:

Endomycorrhizal fungi: *Glomus intraradices, Glomus mosseae, Glomus aggregatum, Glomus clarum, Glomus deserticola, Glomus etunicatum, Gigaspora margarita, Gigaspora brasilianum, Gigaspora monosporum.*

Ectomycorrhizal fungi: *Rhizopogon villosullus, Rhizopogon luteolus, Rhizopogon amylopogon, Rhizopogon fulvigleba, Pisolithus tinctorius, Laccaria bicolor, Laccaria laccata, Scleroderma cepa, Scleroderma citrinum, Suillus granulatas, Suillus punctatapies.*

*Trichoderma* fungi: *Trichoderma harzianum, Trichoderma konigii*

Bacteria: *Bacillus subtillus, Bacillus licheniformis, Bacillus azotoformans, Bacillus megaterium, Bacillus coagulans, Bacillus pumlis, Bacillus thuringiensis, Bacillus stearothermiphilis, Paenibacillus polymyxa, Paenibacillus durum, Paenibacillus florescence, Paenibacillus gordonae, Azotobacter polymyxa, Azotobacter chroococcum, Sacchromyces cervisiac, Streptomyces griseues, Streptomyces lydicus, Pseudomonas aureofaceans, Deinococcus erythromyxa.*

Figure 7A:
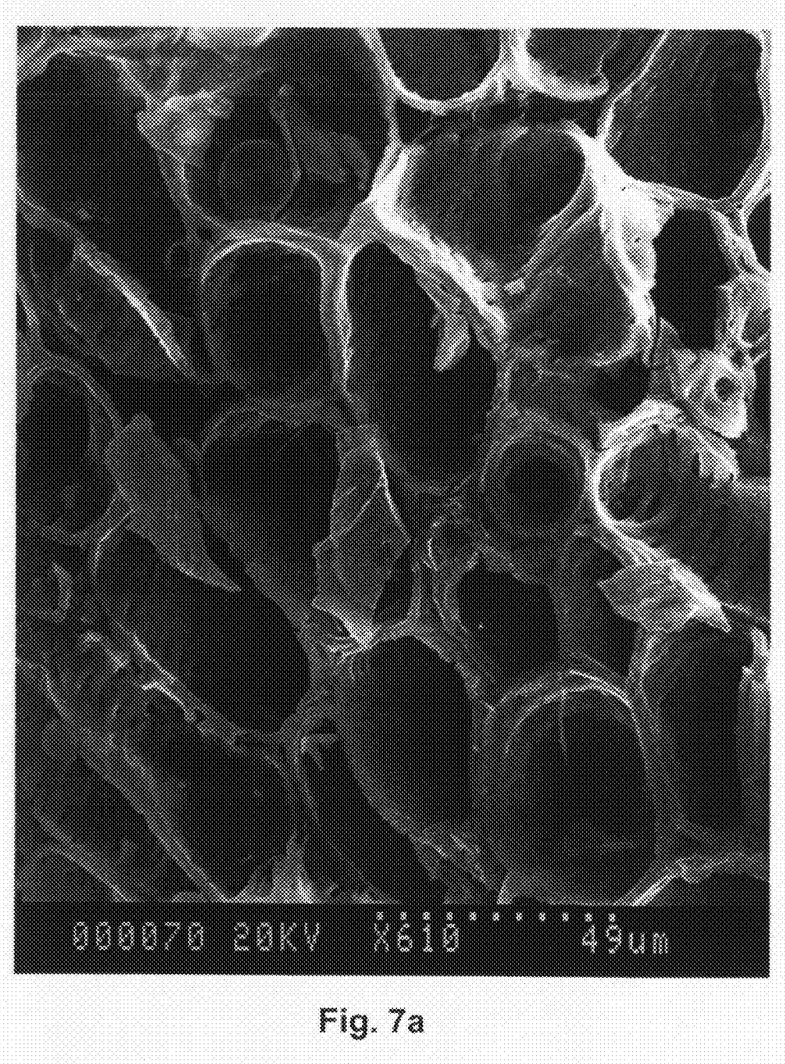
Figure 7B:
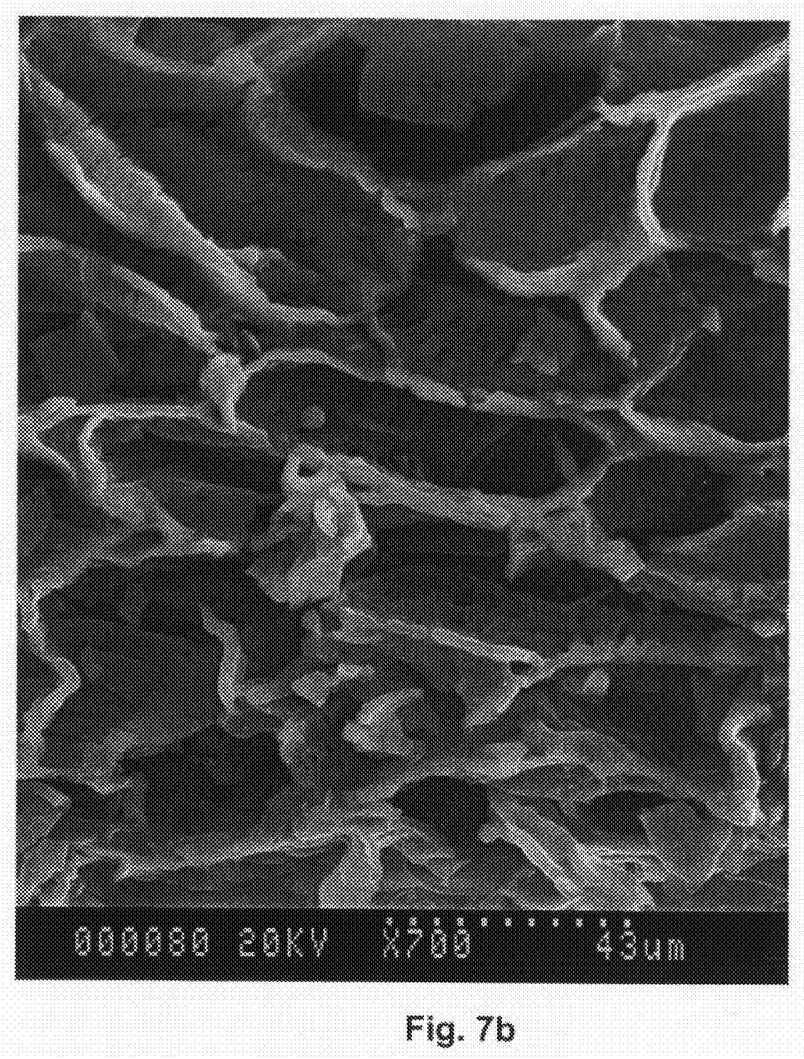
FIG. 7b is an SEM image of BMF char colonized by a commercial compost tea mixture.

BMF char was produced using a biomass fractioning system and made hydrophilic via methods of the present invention. The BMF char was saturated with the above compost mixture in open air for 3 days. An uptake greater than 50% of the dry BMF char weight was observed. The colonization of BMF char derived from corn is shown in the SEM micrograph show in FIG. 7b. Various microorganisms are evident in the micrograph. A comparison of BMF char from a similar derivation but without exposure to microorganisms is shown in FIG. 7a.

Modifications may be made by those skilled in the art without affecting the scope of the invention.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. These illustrations and their accompanying description should not be construed as mandating a particular architecture or configuration.

The invention claimed is:

1. A method for the production of an agent for enhancing soil growth, comprising:
grinding a biomass feedstock to produce ground biomass particles;
subjecting the ground biomass particles to sequential or concurrent ramps of temperature and pressure shocks;
selectively collecting at least one volatile component as it is released from the ground biomass particles;
collecting a last remaining nonvolatile component comprising BMF char;
rendering a surface of the BMF char hydrophilic after collecting the BMF char by removing adsorbed gas within char pores by water infiltration, vacuum suction, ultrasonic means, or impact means;
exposing the BMF char to microorganisms after rendering the surface hydrophilic; and then
adding the BMF char to soil after exposing the BMF char to microorganisms.

2. The method of claim 1, wherein the biomass particles are ground to a diameter between about 0.001 inch and about 1 inch.

3. The method of claim 1, further comprising dispensing the ground biomass particles into thin sheets whose total thickness is a multiple of the ground biomass particle diameter before subjecting the ground biomass particles to sequential or concurrent ramps of temperature and pressure shocks wherein the multiple is any real number in the range of 1 to 30.

4. The method of claim 1, wherein the biomass feedstock is used to produce different BMF chars based on a composition of the biomass feedstock.

5. The method of claim 1, wherein the pressure shocks vary in magnitude from 0.2 MPa to 10 GPa, wherein an admixture of pressure shocks of differing magnitudes is combined with pressure shocks applied over a range of times.

6. The method of claim 1, wherein the temperature ramp includes a sufficiently high temperature to create a nonvolatile carbonaceous material within the ground biomass particles.

7. The method of claim 1, wherein the pressure shocks increase thermal conductivity of formed nonvolatile carbonaceous material within the ground biomass particles.

8. The method of claim 1, wherein the temperature ramps and pressure shocks are conducted in an atmosphere containing a supercritical fluid.

9. The method of claim 1, wherein the pressure shocks decrease the effective density of the ground biomass particles.

10. The method of claim 1, wherein a pH of the BMF char is controlled via pH adjustment agents.

11. The method of claim 1, wherein the BMF char is activated.

12. The method of claim 1, wherein a pH of the soil is modified to accept the addition of BMF char.

13. The method of claim 1, wherein the microorganisms include members of at least one of fungi, bacteria or archaea.

14. The method of claim 13, wherein fungi are members of the phyla Glomeromycota.

15. The method of claim 1, wherein the BMF char contains glomalin structures.

16. A method for the production of an agent for enhancing soil growth, comprising:
grinding a biomass feedstock to produce ground biomass particles having a diameter between about 0.001 inch and about 1 inch;
dispensing the ground biomass particles into thin sheets whose total thickness is a multiple of the ground biomass particle diameter;
subjecting the ground biomass particles to sequential or concurrent ramps of temperature and pressure shocks;
selectively collecting at least one volatile component as it is released from the ground biomass particles;
collecting a last remaining nonvolatile component comprising BMF char;
rendering a surface of the BMF char hydrophilic after collecting the BMF char by removing adsorbed gas within char pores by water infiltration, vacuum suction, ultrasonic means, or impact means;
adding the BMF char to soil after rendering the surface hydrophilic; and then exposing the BMF char to microorganisms.

* * * * *